US011743596B1

United States Patent
Bouvier et al.

(10) Patent No.: US 11,743,596 B1
(45) Date of Patent: Aug. 29, 2023

(54) ADAPTIVE BRIGHTNESS NON-UNIFORMITY CORRECTION IN ENDOSCOPE VISUALIZATION

(71) Applicant: Verily Life Sciences LLC, South San Francisco, CA (US)

(72) Inventors: Aurelien Bouvier, Woodside, CA (US); Nishant Verma, Burlingame, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 296 days.

(21) Appl. No.: 17/322,571

(22) Filed: May 17, 2021

Related U.S. Application Data

(60) Provisional application No. 63/029,319, filed on May 22, 2020.

(51) Int. Cl.
| | | |
|---|---|---|
| *H04N 5/235* | (2006.01) | |
| *A61B 1/00* | (2006.01) | |
| *H04N 23/74* | (2023.01) | |
| *H04N 13/239* | (2018.01) | |

(Continued)

(52) U.S. Cl.
CPC ......... *H04N 23/74* (2023.01); *A61B 1/00006* (2013.01); *A61B 1/00045* (2013.01); *A61B 1/0625* (2022.02); *G06T 7/521* (2017.01); *H04N 13/239* (2018.05); *G06T 2207/10028* (2013.01); *G06T 2207/10068* (2013.01); *G06T 2207/30004* (2013.01)

(58) Field of Classification Search
CPC .. H04N 23/74; H04N 13/239; A61B 1/00006; A61B 1/00045; A61B 1/0625; G06T 7/521; G06T 2207/10028; G06T 2207/10068; G06T 2207/30004

See application file for complete search history.

(56) References Cited

U.S. PATENT DOCUMENTS

| | | | |
|---|---|---|---|
| 6,503,195 B1 * | 1/2003 | Keller | G06T 7/521 |
| | | | 348/45 |
| 7,751,694 B2 * | 7/2010 | Cho | G03B 35/18 |
| | | | 396/17 |
| 2021/0281731 A1 * | 9/2021 | Michihata | H04N 23/75 |

(Continued)

*Primary Examiner* — Howard D Brown, Jr.
(74) *Attorney, Agent, or Firm* — Christensen O'Connor Johnson Kindness PLLC

(57) ABSTRACT

Endoscopic systems, non-transitory, machine-readable storage media, and methods for correcting brightness non-uniformity are described. In an embodiment, the endoscopic system includes a light source positioned to emit illumination light onto a scene; a photodetector positioned to receive illumination light reflected off of the scene and configured to generate a scene signal based on the received illumination light; a display; and a controller operatively coupled to the light source, the photodetector, and the display. In an embodiment, the controller including logic that, when executed by the controller, causes the endoscopic system to perform operations including: illuminating the scene with the light source; detecting a scene depth; estimating a scene-specific brightness non-uniformity correction based on the detected scene depth and an endoscopic system brightness non-uniformity profile; and displaying an image of the scene with the display based on the scene signal, the detected scene depth, and the endoscopic system brightness non-uniformity correction.

20 Claims, 6 Drawing Sheets

(51) Int. Cl.
 *G06T 7/521* (2017.01)
 *A61B 1/06* (2006.01)

(56) References Cited

U.S. PATENT DOCUMENTS

2022/0014660 A1* 1/2022 Zhang ................ A61B 1/00057
2022/0086412 A1* 3/2022 Verma ................. A61B 1/0655

* cited by examiner

ADAPTIVE BRIGHTNESS NON-UNIFORMITY CORRECTION IN ENDOSCOPE VISUALIZATION

CROSS-REFERENCE(S) TO RELATED APPLICATIONS

This application claims the benefit of U.S. Provisional Application No. 63/029,319, filed May 22, 2020, which is hereby incorporated by reference in its entirety.

TECHNICAL FIELD

This disclosure relates generally to endoscopic systems and, in particular but not exclusively, relates to endoscopic systems for correcting brightness non-uniformity.

BACKGROUND INFORMATION

Endoscopes are used in a wide variety of medical procedures, such as laparoscopy, to both illuminate and visualize internal organs of a patient. An endoscope camera feed is frequently displayed on a monitor to guide a physician and clinical staff in conducting such procedures. Many conventional endoscopes provide a 3D stereoscopic view of anatomy in an endoscope field of view by employing two side-by-side cameras that generate left and right eye views for the viewer. The two views are then typically fused either using polarized 3D glasses or an immersive headset viewer.

Image quality from endoscopes is typically affected by a phenomenon called brightness non-uniformity, which refers to a variability in image brightness across the field-of-view unrelated to the objects being imaged. In endoscopes, brightness non-uniformity is a combination of optical vignetting, which naturally occurs in all lenses and typically localized in the periphery of the image, and illumination non-uniformity, which is a variation in illumination across the field-of-view. FIG. 1A shows brightness non-uniformity in an uncorrected image from an endoscope from a combination of optical vignetting and illumination non-uniformity. The illustrated brightness non-uniformity is due, in part, to light drop-off with increasing tissue depth where tissue farther from the endoscope in the back of scene is displayed as generally darker than the tissue close to the endoscope.

Conventional consumer camera and endoscope systems typically correct only for optical vignetting by characterizing the brightness drop-off in image periphery using standardized imaging targets in a bench-top setting and then applying a fixed unit-specific digital correction in the field. The level of optical vignetting is independent of the actual scene being imaged and, therefore, remains constant across different scene depths (i.e. perpendicular distances from a distal end of an imaging device to the objects in a scene). Therefore, such fixed optical vignetting correction produces satisfactory results when vignetting is originating mostly from the optics. However, illumination non-uniformity is significantly more challenging to address because it is scene-dependent and varies with scene.

Such illumination non-uniformity degrades image quality of endoscope systems and limits an ability of health care providers to properly view a scene with sufficient brightness within a field of view of the endoscopic system.

BRIEF DESCRIPTION OF THE DRAWINGS

Non-limiting and non-exhaustive embodiments of the claimed subject matter are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of endoscopic systems, non-transitory, machine-readable storage media, and methods for correcting brightness non-uniformity are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In an aspect, the present disclosure provides endoscopic systems. In that regard, attention is directed to FIGS. 2A and 2B in which an endoscopic system 200, in accordance with an embodiment of the disclosure, is illustrated. As discussed further herein, the systems of the present disclosure, including endoscopic system 200, are suitable to reduce or eliminate non-uniformities in image brightness, in images generated and displayed by the endoscopic systems. Such brightness non-uniformity can result in portions of images being less bright than others due to, for example, optics of the system, distance from an illumination source, at the like.

Figure 2A:
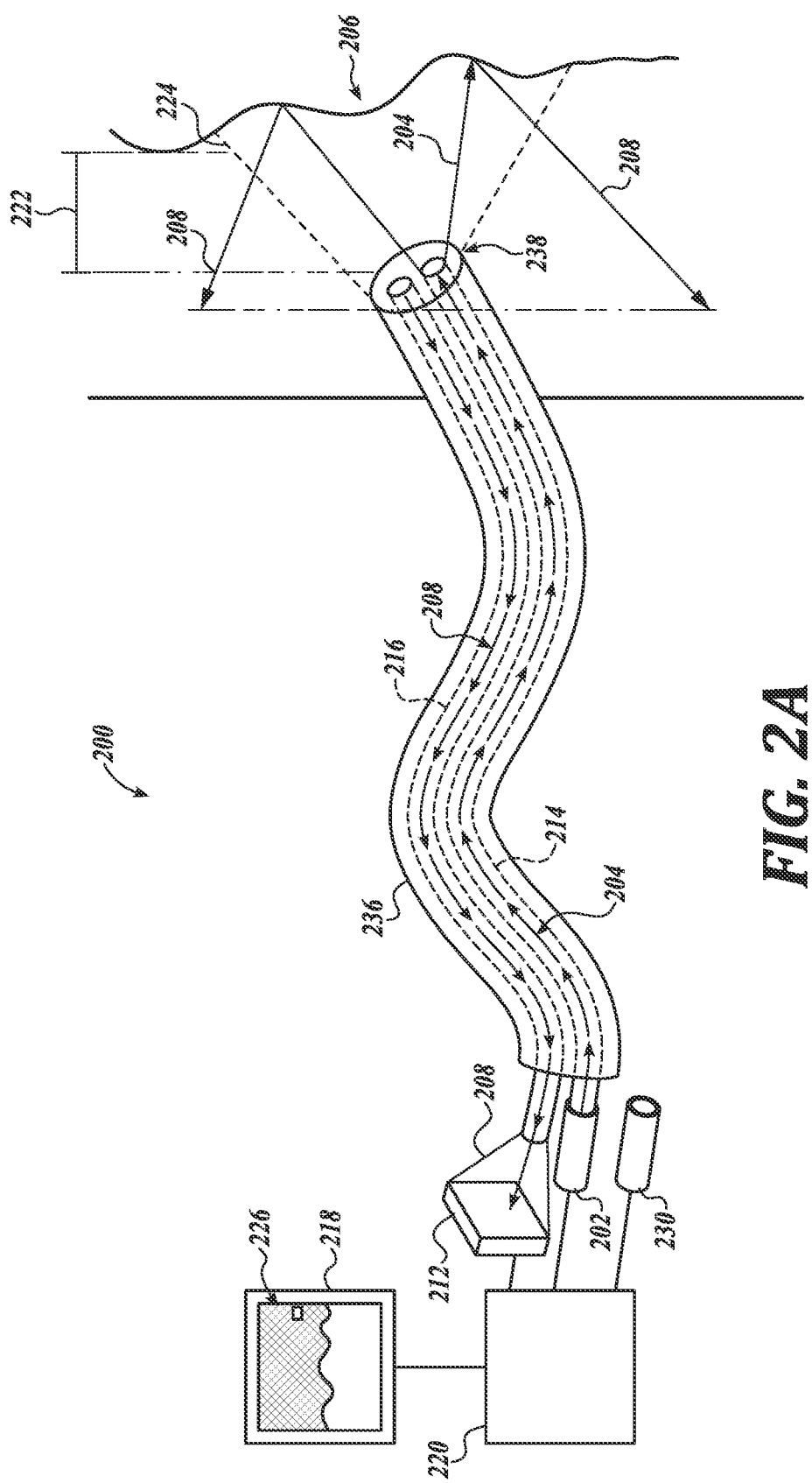
FIG. 2A is a schematic illustration of an endoscopic system, in accordance with an embodiment of the disclosure.

FIG. 2A is a schematic illustration of the endoscopic system 200. As shown, the endoscopic system 200 includes a light source 202 positioned to emit illumination light 204 onto a scene 206; a photodetector 212 positioned to receive illumination light reflected off of the scene 206; a display 218; and a controller 220 operatively coupled to the light source 202, the photodetector 212, and the display 218 to choreograph their operation. In an embodiment, the controller 220 includes logic that, when executed by the controller 220, causes the endoscopic system 200 to perform operations, such as to perform one or more of the methods of the present disclosure, such as one or more of methods 400 and 500 discussed further herein.

The endoscopic system 200 is shown to further include an endoscope 236 positioned to transmit illumination light 204 from the light source 202 through an illumination light pipe 214 of the endoscope 236 and emit the illumination light 204 from a distal end 238 of the endoscope 236 and onto the scene 206. In an embodiment, the endoscope 236 is configured to enter into and image a surgical scene 206, such as a surgical scene 206 within a body of a patient. The endoscope 236 further includes a photodetection light pipe 216 positioned to receive reflected illumination light 208 reflected off of the scene 206 and transmit the reflected illumination light 208 through the photodetection light pipe 216 to be emitted from a proximal end of the endoscope 236. As shown, the photodetector 212 is positioned adjacent to the proximal end of the endoscope 236 to receive the reflected illumination light 208 from the proximal end of the photodetection light pipe 216.

While the photodetector 212 is positioned adjacent to the proximal end of the endoscope 236 in the illustrated embodiment, in some embodiments, the photodetector 212 is positioned at the distal end 238 of the endoscope 236 to directly image the scene 206.

The photodetector 212 is responsive to the illumination light 204 and is configured to generate a scene signal based on the reflected illumination light 208. As discussed further herein with respect to the methods of the present disclosure, the scene signal is suitable for use in generating an image 226 of the scene 206, such as for displaying with the display 218. The photodetector 212 can be any photodetector 212 suitable to generate a scene signal based on or responsive to the received illumination light 204, such as reflected illumination light 208.

Figure 2B:
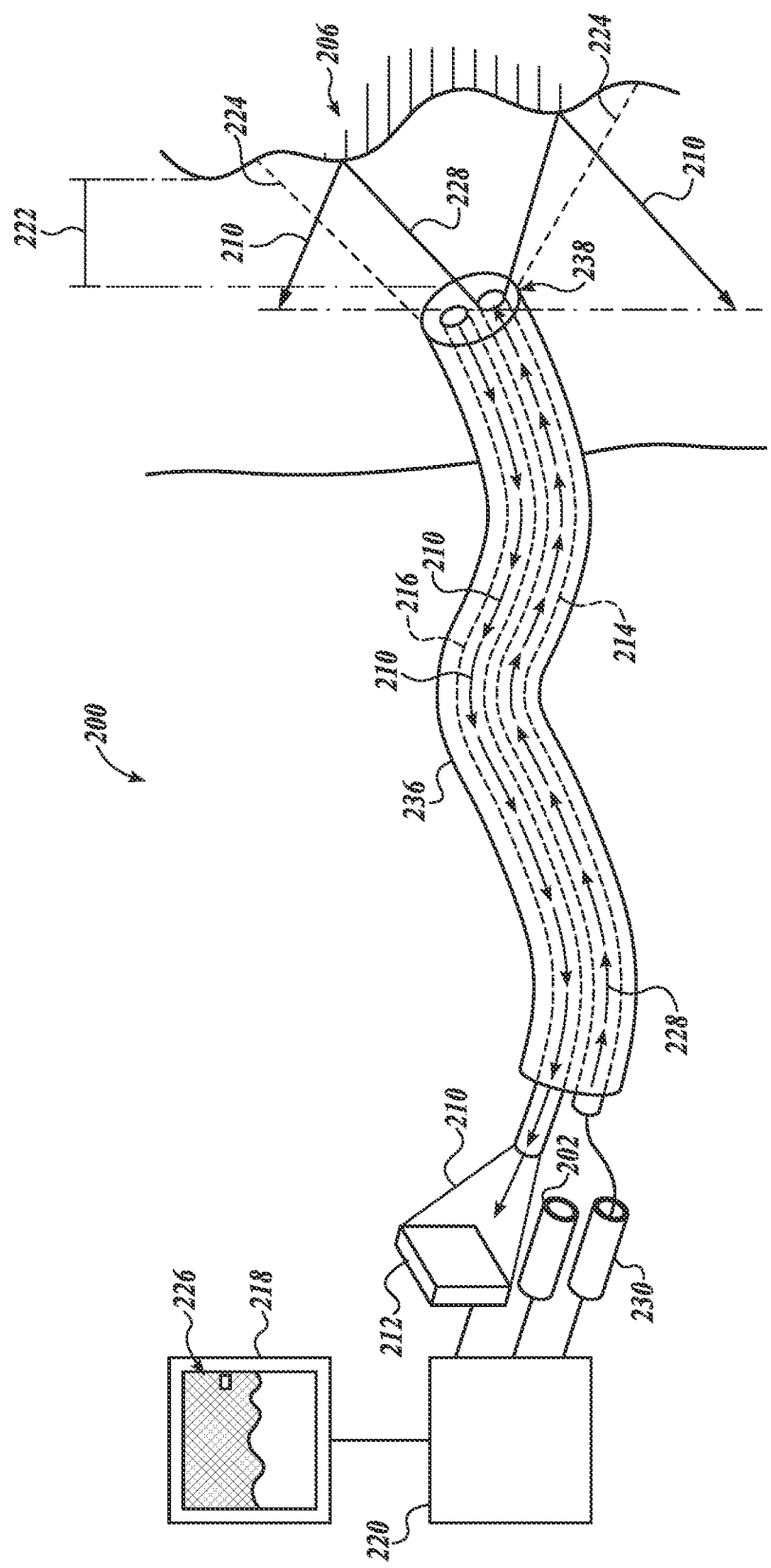
FIG. 2B is another schematic illustration of the endoscopic system of FIG. 2A, in accordance with an embodiment of the disclosure.

FIG. 2B is another schematic illustration of the endoscopic system 200 of FIG. 2A, in accordance with an embodiment of the disclosure, illustrating the endoscopic system 200 emitting structured light 228 onto the scene 206. In the illustrated embodiment, the endoscopic system 200 is shown to include a structured light source 230 configured to emit the structured light 228. As used herein, "structured light" refers to light having a known pattern. In an embodiment, the structured light 228 includes one or more grids, bars, dots, and the like. As shown, the portion of the scene 206 illuminated by the structured light 228 includes a series of lines of the structured light 228. While a series of lines are shown, other forms of structured light 228 are within the scope of the present disclosure. As discussed further herein with respect to the methods of the present disclosure, such structured light 228 may be used to determine a scene depth 222, such as based on deformation of the known pattern as it is reflected off of the scene 206 and comparing the deformation of the known pattern with the known pattern.

In an embodiment, the endoscopic system 200 is configured to emit the illumination light 204 in a first time interval; and emit the structured light 228 in a second time interval different from and not overlapping with the first time interval. As shown in FIG. 2A, the endoscopic system 200 emits the illumination light 204 at a time when the structured light 228 is not emitted. Correspondingly, as shown in FIG. 2B, the endoscopic system 200 emits the structured light 228 at a time when the illumination light 204 is not emitted. As discussed further herein with respect to the methods of the present disclosure, the photodetector 212 is configured to generate a scene signal based on illumination light 204 received by the photodetector 212, such as reflected illumination light 208. Additionally, the endoscopic system 200 is configured to detect a scene depth 222 across a field of view 224 based upon a structured light signal of the photodetector 212 generated during the second time interval and based on reflected structured light 210. In this regard, by alternating between emitting illumination light 204 and structured light 228, the endoscopic system 200 is configured to both generate an image 226 of the scene 206 and detect a scene depth 222 suitable for use in estimating a scene-specific brightness non-uniformity correction. Further, by emitting structured light 228 during a time interval when the photodetector 212 is not generating a scene signal (e.g. the second time interval), the image 226 of the scene 206 does not include features based on the structured light 228, which might distract a viewer or occlude certain scene 206 details.

In an embodiment, the structured light 228 includes non-visible light, such as infrared light, ultraviolet light, and the like. In an embodiment, the photodetector 212 is responsive to and configured to generate a structured light signal based on this non-visible structured. Non-visible structured light 228 is suitable in determining a scene depth 222 while not being visible, such as in an image 226 displayed by the display 218. In this regard, the non-visible structured light 228 does not obscure aspects of a displayed scene 206 or distract a user in viewing the scene 206 on the display 218. In an embodiment, the endoscopic system 200 is configured to emit the illumination light 204 and the non-visible structured light 228 simultaneously.

While the endoscopic system 200 is shown to include a structured light source 230 configured to emit structured light 228, in an embodiment, the illumination light source 202 is configured to emit structured light 228 onto the scene 206, such as by emitting structured light 228 through the illumination light pipe 214. In such an embodiment, the structured light source 230 is optional or may be omitted.

Figure 3:
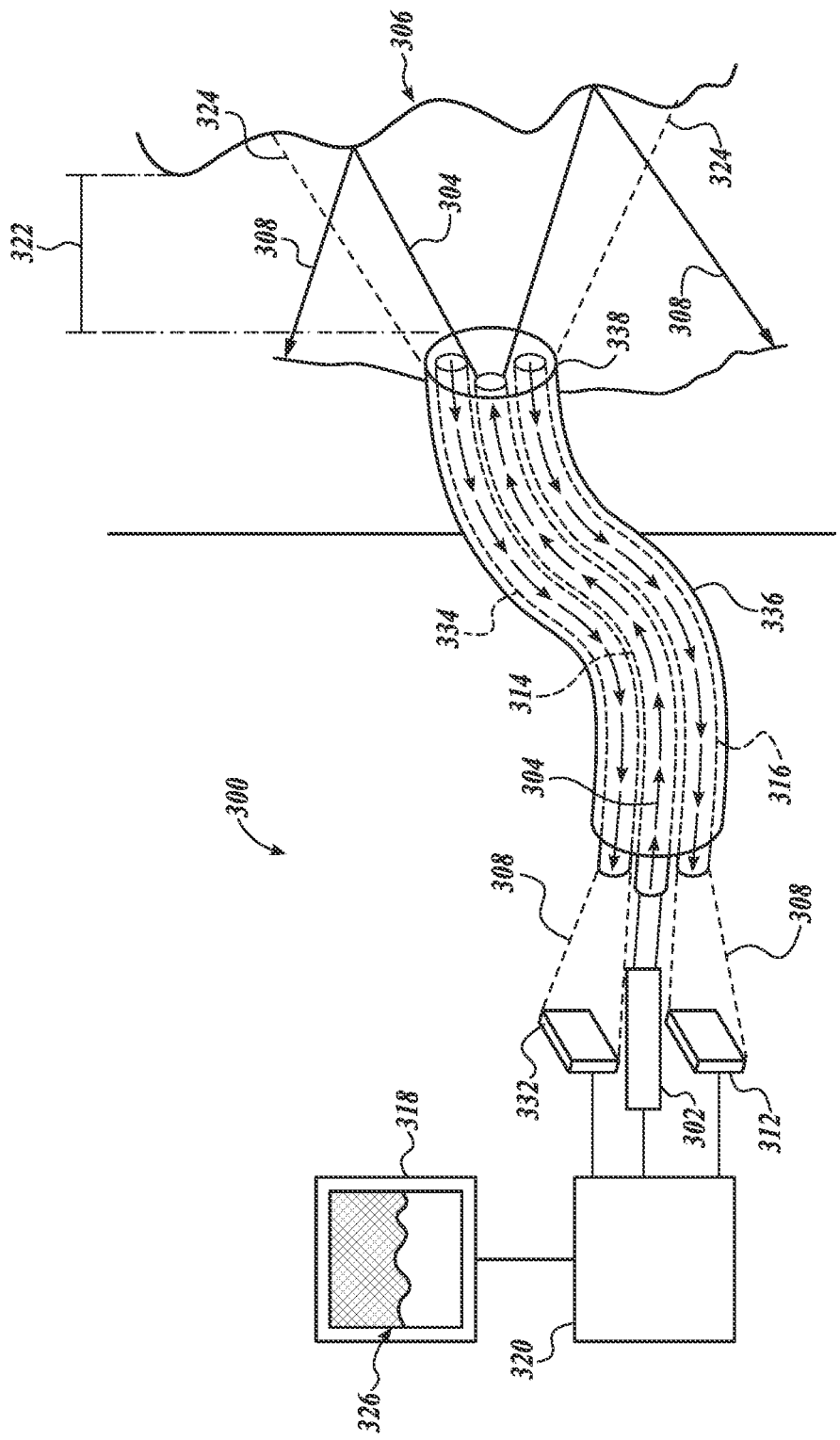
FIG. 3 is a schematic illustration of an endoscopic system, in accordance with an embodiment of the disclosure.

FIG. 3 is a schematic illustration of another endoscopic system 300, in accordance with an embodiment of the disclosure. The endoscopic system 300 is shown to include a light source 302 positioned to emit illumination light 304 onto a scene 306; a first photodetector 312 and a second photodetector 332 each positioned to receive illumination light reflected off of the scene 306; a display 318 configured to display an image 326, such as an image 326 of the scene 306; and a controller 320 operatively coupled to the light source 302, the photodetectors 312 and 332, and the display 318 to choreograph their operation. In an embodiment, the controller 320 includes logic that, when executed by the controller 320, causes the endoscopic system 300 to perform operations, such as one or more of the methods of the present disclosure, such as methods 400 and 500.

The first photodetector 312 is configured to generate a first scene signal based on the received illumination light, and the second photodetector 332 is configured to generate a second scene signal based on the reflected illumination light 308. As discussed further herein, such first and second scene signals are suitable for generating an image 326 of the scene 306 for the display 318 and for determining a scene depth 322.

As shown, the endoscopic system 300 includes an endoscope 336 configured to transmit and receive light between a proximal end of the endoscope 336 and a distal end 338 of the endoscope 336. In an embodiment, the endoscope 336 is sized and shaped to enter into a portion of a body of a patient, such as into a surgical scene 306 to image the scene 306. In the illustrated embodiment, the endoscope 336 includes an illumination light pipe 314 positioned to transmit illumination light 304 from the light source 302 and to emit the illumination light 304 onto the scene 306. The endoscope 336 is shown to further include a first photodetection light pipe 316 positioned to receive a portion of reflected illumination light 308 and to transmit the reflected illumination light 308 onto the first photodetector 312. As shown, the endoscope 336 includes a second photodetection light pipe 334 positioned to receive a second portion of the reflected illumination light 308 and to transmit the second portion of the reflected illumination light 308 onto the second photodetector 332. In this regard, the endoscopic system 300 is configured to generate first and second scene signals with the first and second photodetectors 312 and 332, respectively, based on different portions of reflected illumination light 308. As discussed further herein, such a configuration is suitable to determine a scene depth 322 of the endoscopic system 300 and to generate an image 326, such as a stereoscopic image 326, of the scene 306 for the display 318.

While the photodetectors 312 and 332 are shown positioned adjacent to a proximal end of the endoscope 336, in some embodiments, the photodetector 312 and 332 are positioned at or adjacent to the distal end 338 of the endoscope 336 to directly image the scene 306.

As shown, the first photodetection light pipe 316 and the second photodetection light pipe 334 are separated by a distance at the distal end 338 of the endoscope 336. In this regard, the first and second photodetectors 312 and 332 are shaped and positioned to receive reflected illumination light 308 received by spatially separate portions of the distal end 338 of the endoscope 336. As discussed further herein with respect to the methods of the present disclosure, such a configuration is suitable to generate a depth map useful in detecting the scene depth 322 across the field of view 324 of the endoscopic system 300.

In another aspect, the present disclosure provides methods for correcting brightness non-uniformity of an endoscopic system. Such methods for correcting brightness non-uniformity of an endoscopic system will now be discussed with respect to FIGS. 4 and 5.

Figure 1A:
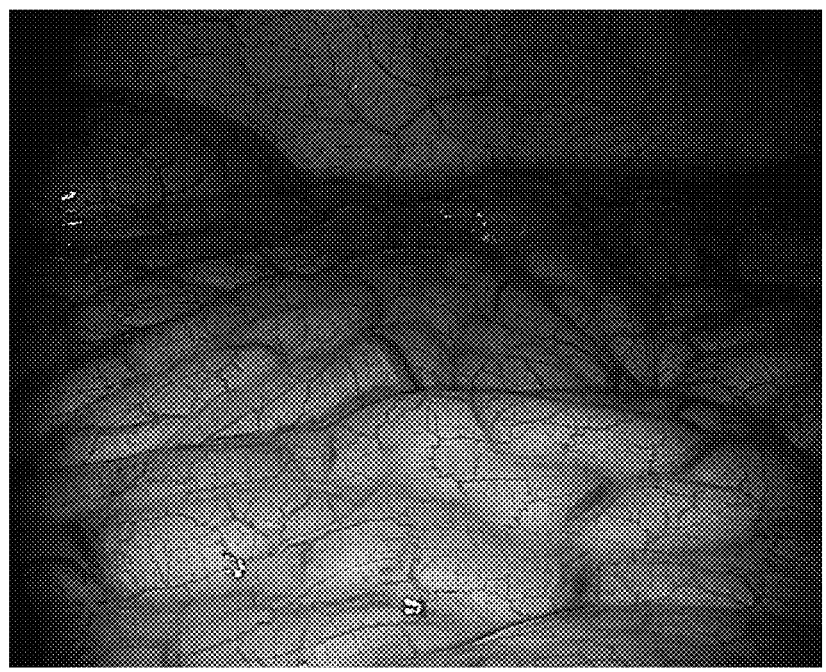
FIG. 1A is an uncorrected image of a surgical scene from an endoscopic system.
Figure 1B:
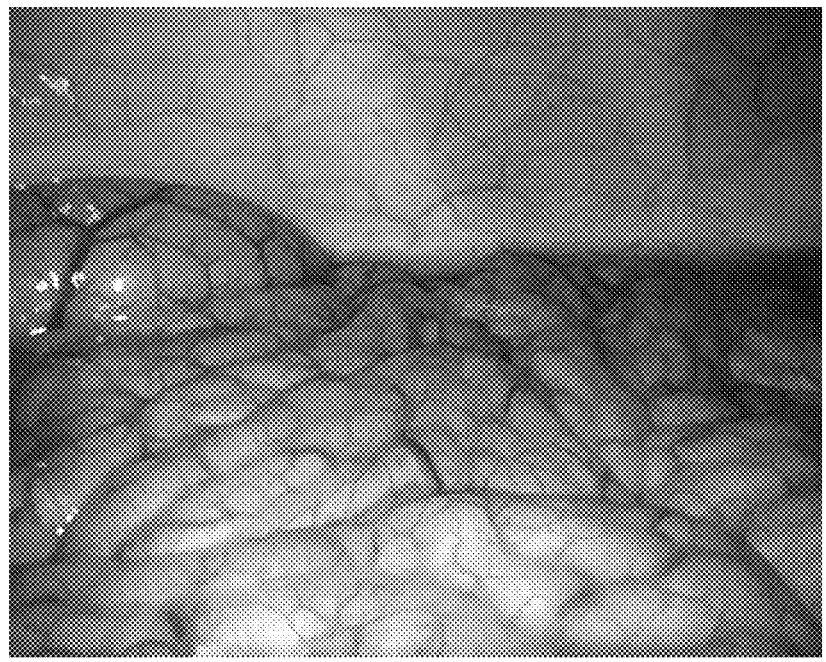
FIG. 1B is a corrected version of the image from FIG. 1A, in accordance with an embodiment of the disclosure.
Figure 4:
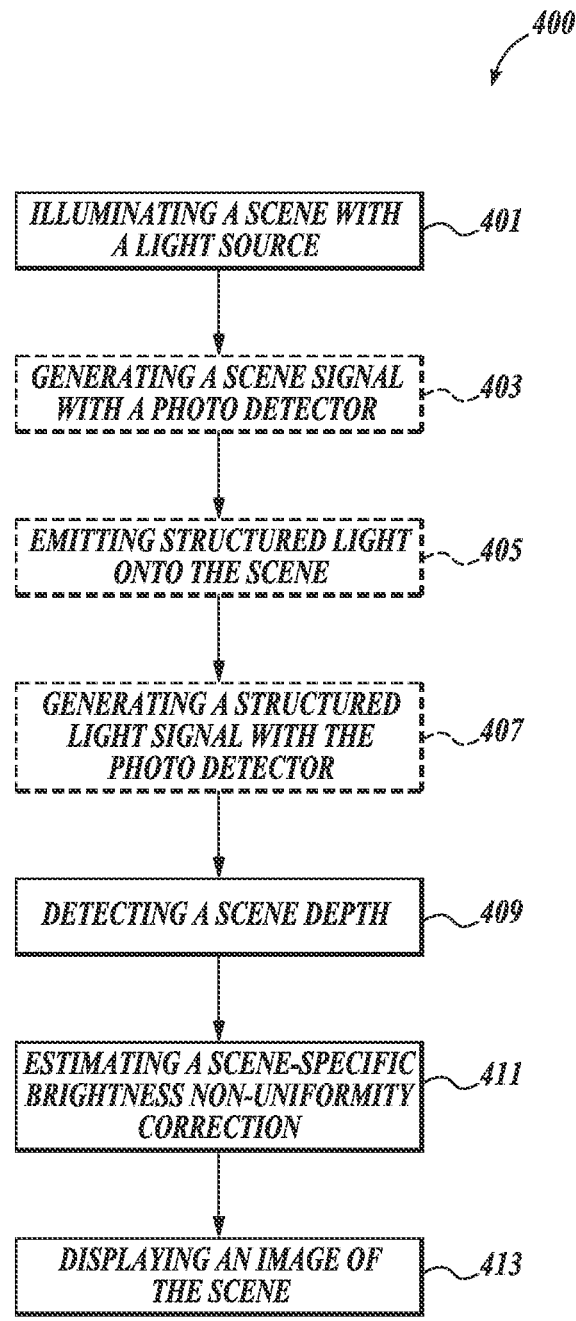
FIG. 4 is a block diagram of a method for correcting brightness non-uniformity of an endoscopic system, in accordance with an embodiment of the disclosure.

FIG. 4 is a block diagram of a method 400 for correcting brightness non-uniformity of an endoscopic system, in accordance with an embodiment of the disclosure. As above, brightness non-uniformity can obscure or darken portions of an imaged scene, as shown in FIG. 1A. Correction applied to images of imaging devices, such as endoscopic systems of the present disclosure, can more fully illuminate an imaged scene for clear viewing, such as is shown in FIG. 1B.

In an embodiment, the method 400 is suitable for operating an endoscopic system of the present disclosure, such as endoscopic systems 200 and 300 discussed further herein with respect to FIGS. 2A and 2B and FIG. 3, respectively, to correct brightness non-uniformity of images generated by the endoscopic systems 200 and 300. In an embodiment, the method 400 is suitable for operating endoscopic system 200 discussed further herein with respect to FIG. 2A and 2B, to correct brightness non-uniformity of images generated by the endoscopic system 200.

In an embodiment, the method 400 begins with process block 401, which includes illuminating a scene with a light source, such as with light sources 202 or 302. Such illumination can include illumination with illumination light suitable to illuminate a scene, such as a surgical scene. In an embodiment, the illumination light includes visible light, infrared light, ultraviolet light, and combinations thereof.

In an embodiment, process block 401 is followed by process block 403, which includes generating a scene signal with a photodetector based on illumination light reflected off of the scene. As discussed further herein, such a scene signal may be used in displaying an image of the scene based on the scene signal. In an embodiment, generating a scene signal includes generating a signal at one or more pixels of a photodetector, such as at all pixels of the photodetector. In this regard, the scene signal(s) is/are based on light reflected off of multiple portions of the scene and is/are suitable for generating an image based on the scene viewable within an endoscopic system field of view. In an embodiment, process block 403 is optional.

In an embodiment, process block 401 or 403 are followed by process block 405, which includes emitting structured light onto the scene. In an embodiment, the structured light is emitted from an illumination light source also used to emit the illumination light. In an embodiment, the structured light is emitted from a structured light source distinct from an illumination light source. In an embodiment, the structured light includes a known pattern, such as a grid, dots, lines, concentric circles, and the like. In an embodiment, process block 405 is optional.

In an embodiment, the structured light is non-visible light, such as light excluding light having wavelengths in a visible range (e.g. between about 400 nm and about 700 nm). In an embodiment, the structured light includes infrared light, ultraviolet light, and combinations thereof. In this regard, the non-visible structured light is not visible to a viewer viewing an image on the display. Accordingly, with non-visible structured light, the image of the scene does not include or is not based upon the structured light, which might distract a viewer from aspects of the scene or occlude or obscure the viewer from seeing such aspects.

In an embodiment, process block 405 is followed by process block 407, which includes generating a structured light signal with a photodetector. In an embodiment, the photodetector is the same photodetector used to generate the scene signal. In an embodiment, the photodetector used to generate the structured light signal is a different photodetector than the photodetector used to generate the scene signal, such as where the scene signal is based on visible light and where the structured light signal is based upon non-visible light. In an embodiment, process block 407 is optional.

In an embodiment, process block 401, 403, 405, or 407 is/are followed by process block 409, which includes detecting a scene depth. In an embodiment, a scene depth is a distance between a distal end of an endoscope of the endoscopic system and a feature of the scene within the endoscopic system field of view, such as where the photodetector is positioned at a proximal end of the endoscope. In an embodiment, the scene depth is a distance between the photodetector and features of the scene, such as where the photodetector is positioned at a distal end of the endoscope.

In an embodiment, detecting the scene depth across the field of view is based upon structured light reflected off of the scene, such as structured light emitted as part of process block 405. In an embodiment, distortions between the original light pattern of the structured light and the reflected pattern observed by the photodetector are used to determine the scene depth, such as by comparing the distortions of the known pattern with the known pattern.

In an embodiment, emitting the illumination light, such as in process block 401, is in a first time interval; and emitting the structured light, such as in process block 405, is in a second time interval not overlapping with the first time interval. Correspondingly, in an embodiment, generating the scene signal, such as in process block 403, includes generating the scene signal with the photodetector generated during the first time interval and generating the structured light signal, such as in process block 407, is in the second time interval. In this regard, the scene signal used to generate an image of the scene does not include and/or is not based on the structured light signals, which might obscure or occlude features of the scene. In an embodiment, detecting the scene depth across the field of view is based upon a structured light signal of the photodetector generated during the second time interval.

In an embodiment, a scene depth is estimated for every pixel of the photodetector. In this regard, a scene depth can be estimated across the endoscopic system field of view and a scene depth can be estimated between, for example, a distal end of an endoscope of the endoscopic system and various scene features.

In an embodiment, process blocks 401 and 403 are followed by process blocks 405 and 407 and are repeated to generate a video feed for displaying a video image of the scene on a display and to estimate a scene-specific brightness non-uniformity correction of the video image, as discussed further herein.

In an embodiment, process block 409 is followed by process block 411, which includes estimating a scene-specific brightness non-uniformity correction based on the detected scene depth, such as from process block 409, and an endoscopic system brightness non-uniformity profile.

In an embodiment, the endoscopic system brightness non-uniformity profile is based on a plurality of images generated by the photodetector with varying scene depths and varying orientations within the endoscopic system field of view. In an embodiment, the endoscopic system brightness non-uniformity profile is generated by capturing still images with the endoscopic system of a white diffused target at several discrete orientations and working distances spanning an entire working distance range of the endoscopic system. As an example, if a specified working distance range of the endoscopic system is 20-120 mm, then images of a white diffused target may be captured at discrete working distances of, for example, in 10 mm steps spanning the working distance range (i.e. 20 mm, 30 mm, 40 mm, etc. up to 120 mm) and at orientation angles between −90° and 90° at 30° intervals (i.e. −90°, −60°, −30°, 0°, 30°, 60° and 90° . While particular working distance ranges, orientation angles, and intervals of such metrics are described, it will be understood that other working distance ranges, orientation angles, and intervals are within the scope of the present disclosure.

In an embodiment, once the scene depth is determined, an endoscopic system brightness non-uniformity profile for that scene depth is selected and applied to estimate the scene-specific brightness non-uniformity correction.

In an embodiment, the endoscopic system brightness non-uniformity profile is based on empirically estimating endoscopic system brightness non-uniformity, such as with white diffused target oriented perpendicular to the endoscope's optical axis at a nominal scene depth and extrapolating to other working distances using a theoretical estimate of illumination drop-off with distance. In an embodiment, the effective illumination per unit area on a surface drops off by a factor of $D^2$ where D is the distance of the object from illumination source (i.e. a scene depth).

In an embodiment, process block 411 is followed by process block 413, which includes displaying an image of the scene with a display, such as a display of the endoscopic system. In an embodiment, the image is based on the scene signal, the detected scene depth, and the scene-specific brightness non-uniformity correction. In an embodiment, displaying the image of the scene includes adjusting raw image data based on or including the scene signal with a digital scene-specific brightness non-uniformity correction. In this regard, the displayed image is corrected for endoscopic system vignetting and as well as scene depth.

Such a correction is illustrated in FIGS. 1A and 1B in which an uncorrected image of a surgical scene is shown in FIG. 1A and a corrected version of the image of FIG. 1A is shown in FIG. 1B. As shown, the image shown in FIG. 1B is better illuminated throughout the depth of field of the image and around the periphery of the image.

Figure 5:
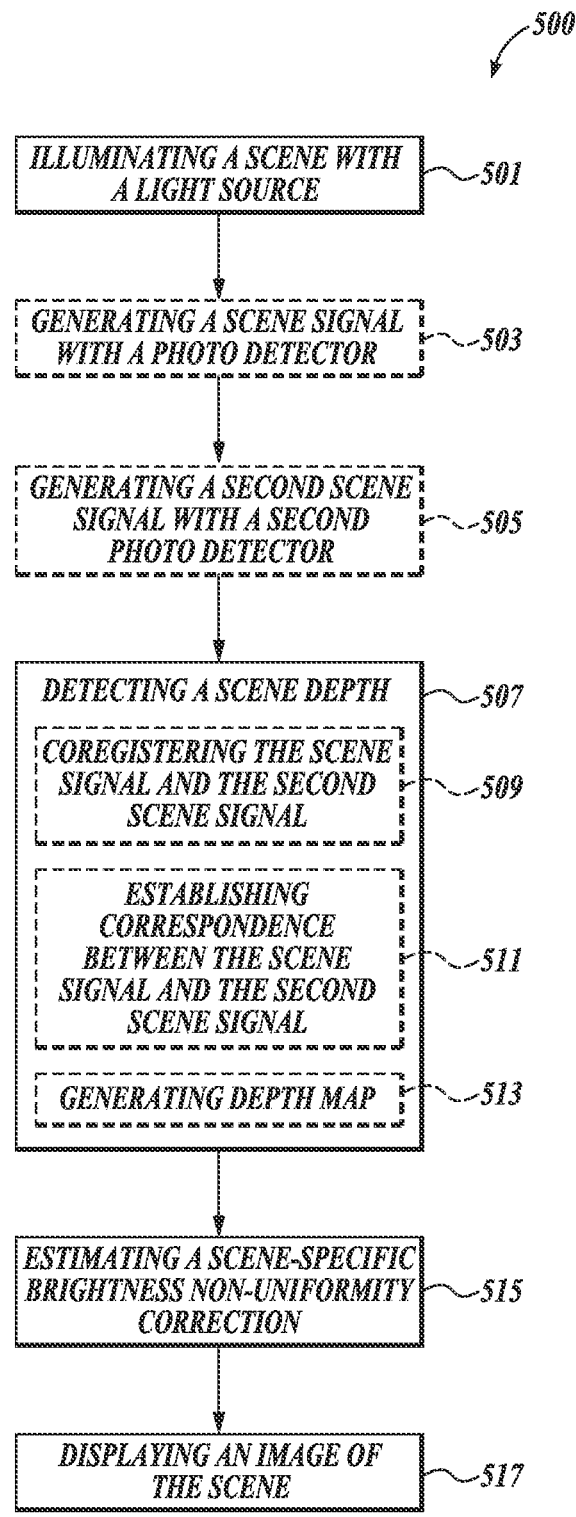
FIG. 5 is a block diagram of a method for correcting brightness non-uniformity of an endoscopic system, in accordance with an embodiment of the disclosure.

FIG. 5 is a block diagram of a method 500 for correcting brightness non-uniformity of an endoscopic system, in accordance with an embodiment of the disclosure. In an embodiment, the method 500 is a method 500 for operating the endoscopic systems 200 or 300 discussed further herein with respect to FIGS. 2A, 2B, and 3. In an embodiment, the method 500 is a method 500 for operating endoscopic system 300, discussed further herein with respect to FIG. 3.

In an embodiment, the method 500 begins with process block 501, which includes illuminating a scene with a light source, such as a light source of the endoscopic system. In an embodiment, illuminating the scene includes emitting illumination light from the light source.

In an embodiment, process block 501 is followed by process block 503, which includes generating a scene signal with a photodetector, such as a photodetector of the endoscopic system. In an embodiment, the scene signal is based on reflected illumination light reflected off of the scene, such as reflected illumination light that impinges upon the photodetector, wherein the photodetector is responsive to and generates the scene signal in response to the impinging reflected illumination light. In an embodiment, generating the scene signal with the photodetector includes generating scene signal at every pixel of the photodetector, thereby generating a scene signal based on reflected illumination light across an endoscope field of view. In an embodiment, process block 503 is optional.

In an embodiment, process block 503 is followed by process block 505, which includes generating a second scene signal with a second photodetector. In an embodiment, the second photodetector is positioned receive reflected illumination light that is different from the reflected illumination light received by the photodetector in process block 503. For example, as shown in FIG. 3, the first and second photodetection light pipes 316 and 334 terminate at different positions at the distal end 338 of the endoscope 336 and, in this regard, are positioned to receive different portions of reflected illumination light 308 reflected off of the scene 306. In an embodiment, generating the second scene signal includes generating second scene signal at every pixel of the second photodetector, thereby generating a scene second signal based on reflected illumination light across an endoscope field of view. In an embodiment, process block 505 is optional.

In an embodiment, process blocks 501, 503, or 505 are followed by process block 507, which includes detecting a scene depth across an endoscopic system field of view. In an embodiment, process block 507 includes process sub-block 509, which includes co-registering the first scene signal and the second scene signal. In an embodiment, co-registering the first scene signal and the second scene signal includes image processing and machine learning to establish correspondence between the pixels of the first photodetector and the second photodetector. In an embodiment, process sub-block 509 is optional.

In an embodiment, process block 507 includes process sub-block 511, which includes establishing a correspondence between the first scene signal and the second scene signal. In an embodiment, process sub-block 511 is optional.

In an embodiment, process block 507 includes process sub-block 513, which includes generating a depth map based on the first scene signal and the second scene signal. In an embodiment, the depth map is based on pixel coordinates of pixels of the first photodetector and the second photodetector, an offset distance between the pixels of the first photodetector and the second photodetector, a distance between the first photodetector and the second photodetector, and a focal distance of the endoscopic system. In an embodiment, the depth map is calculated at every pixel location of the first and second photodetectors. In an embodiment, process block 513 is optional.

In an embodiment, process block 507 is followed by process block 515, which includes estimating a scene-specific brightness non-uniformity correction. In an embodiment, estimating the scene-specific brightness non-uniformity correction includes: estimating a first scene-specific brightness non-uniformity correction based on a detected first scene depth of the first photodetector and a first scene-specific brightness non-uniformity profile of the first photodetector; and estimating a second scene-specific brightness non-uniformity correction based on a detected second scene depth of the second photodetector and a second scene-specific brightness non-uniformity profile of the second photodetector, such as generated in process sub-blocks 509, 511, and 513.

In an embodiment, the scene-specific brightness non-uniformity correction is based on the detected scene depth, such as detected in process block 507, and a scene-specific brightness non-uniformity profile.

In an embodiment, the endoscopic system brightness non-uniformity profile is based on a plurality of images generated by the photodetector with varying scene depths and varying orientations within the endoscopic system field of view. In an embodiment, the endoscopic system brightness non-uniformity profile is generated by capturing still images with the endoscopic system of a white diffused target at several discrete orientations and working distances spanning an entire working distance range of the endoscopic system. As an example, if a specified working distance range of the endoscopic system is 20-120 mm, then images of a white diffused target may be captured at discrete working distances of, for example, in 10 mm steps spanning the working distance range (i.e. 20 mm, 30 mm, 40 mm, etc. up to 120 mm) and at orientation angles between −90° and 90° at 30° intervals (i.e. −90°, −60°, −30°, 0°, 30°, 60° and 90°. In an embodiment, once the scene depth is determined, an endoscopic system brightness non-uniformity profile for that scene depth is selected and applied to estimate the scene-specific brightness non-uniformity correction.

In an embodiment, the endoscopic system brightness non-uniformity profile is based on empirically estimating system brightness non-uniformity, such as with white diffused target oriented perpendicular to the endoscope's optical axis, at a nominal scene depth and extrapolating to other working distances using a theoretical estimate of illumination drop-off with distance. In an embodiment, the effective illumination per unit area on a surface drops off by a factor of $D^2$ where D is the distance of the object from illumination source (i.e. scene depth).

In an embodiment, process block 515 is followed by process block 517, which includes displaying an image of the scene, such as with a display of the endoscopic system. In an embodiment, the image is based upon the first and second scene signals, the detected scene depth, and the scene-specific brightness non-uniformity correction. In an embodiment, displaying the image of the scene includes adjusting raw image data based on or including the scene signal with the digital scene-specific brightness non-uniformity correction.

The order in which some or all of the process blocks appear in each process should not be deemed limiting. Rather, one of ordinary skill in the art having the benefit of the present disclosure will understand that some of the process blocks may be executed in a variety of orders not illustrated, or even in parallel.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

In another aspect, the present disclosure provides non-transitory, machine-readable storage medium for performing one or more of the methods of the present disclosure, such as methods 400 and 500 discussed further herein with respect to FIGS. 4 and 5, respectively. In an embodiment, the provided non-transitory, machine-readable storage medium is suitable for performing the methods of the present disclosure with the endoscopic systems of the present disclosure, such as endoscopic systems 200 and 300.

In an embodiment, the non-transitory, machine-readable storage medium have instructions stored thereon, which when executed by a processing system, cause the processing system to perform operations comprising: illuminating a scene with a light source of an endoscopic system; generating a scene signal with a photodetector based on illumination light reflected off of the scene; detecting a scene depth across an endoscopic system field of view; estimating a scene-specific brightness non-uniformity correction based on the detected scene depth and a scene-specific brightness non-uniformity profile; and displaying an image of the scene with a display of the endoscopic system based on the scene signal, the detected scene depth, and the scene-specific brightness non-uniformity correction.

In an embodiment, the non-transitory, machine-readable storage medium includes instructions stored thereon, which when executed by a processing system, cause the processing system to perform operations comprising: emitting structured light from the light source, wherein detecting the scene depth across the field of view is based upon structured light reflected off of the scene. In an embodiment, the structured light includes non-visible light.

In an embodiment, the non-transitory, machine-readable storage medium includes instructions stored thereon, which when executed by a processing system, cause the processing system to perform operations comprising: emitting the illumination light in a first time interval; and emitting the structured light in a second time interval not overlapping with the first time interval.

In an embodiment, detecting the scene depth across the field of view of the endoscopic system includes co-registering a first scene signal of the photodetector and a second scene signal of a second photodetector of the endoscopic system; establishing a correspondence between the first scene signal and the second scene signal; and generating a depth map based on the first scene signal and the second scene signal.

A tangible machine-readable storage medium, such as a non-transitory, machine-readable storage medium, includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An endoscopic system comprising:
a light source positioned to emit illumination light onto a scene;
a photodetector positioned to receive illumination light reflected off of the scene and configured to generate a scene signal based on the received illumination light;
a display; and
a controller operatively coupled to the light source, the photodetector, and the display, the controller including logic that, when executed by the controller, causes the endoscopic system to perform operations including:
illuminating the scene with the light source;
detecting a scene depth across an endoscopic system field of view;
estimating a scene-specific brightness non-uniformity correction based on the detected scene depth and an endoscopic system brightness non-uniformity profile; and
displaying an image of the scene with the display based on the scene signal, the detected scene depth, and the scene-specific brightness non-uniformity correction.

2. The endoscopic system of claim 1, wherein the controller further includes logic that, when executed by the controller causes the endoscopic system to perform operations including:
emitting structured light from the light source, wherein detecting the scene depth across the field of view is based upon structured light reflected off of the scene.

3. The endoscopic system of claim 2, wherein the structured light includes non-visible light.

4. The endoscopic system of claim 2, wherein the controller further includes logic that, when executed by the controller causes the endoscopic system to perform operations including:
emitting the illumination light in a first time interval; and
emitting the structured light in a second time interval not overlapping with the first time interval.

5. The endoscopic system of claim 4, wherein detecting the scene depth across the field of view is based upon a structured light signal of the photodetector generated during the second time interval.

6. The endoscopic system of claim 1, further comprising a structured light source operatively coupled to the controller, the structured light source configured to emit structured light onto the scene, wherein the controller further includes logic that, when executed by the controller causes the endoscopic system to perform operations including:
emitting structured light from the structured light source, wherein detecting the scene depth across the field of view is based upon structured light reflected off of the scene.

7. The endoscopic system of claim 1, wherein the photodetector is a first photodetector and the scene signal is a first scene signal, wherein the endoscopic system further comprises a second photodetector positioned receive illumination light reflected off of the scene and configured generate a second scene signal based on the received illumination light.

8. The endoscopic system of claim 7, wherein detecting the scene depth across the field of view of the endoscopic system includes co-registering the first scene signal and the second scene signal; establishing a correspondence between the first scene signal and the second scene signal; and generating a depth map based on the first scene signal and the second scene signal.

9. The endoscopic system of claim 8, wherein the depth map is based on pixel coordinates of pixels of the first photodetector and the second photodetector, an offset distance between the pixels of the first photodetector and the second photodetector, a distance between the first photodetector and the second photodetector, and a focal distance of the endoscopic system.

10. The endoscopic system of claim 8, wherein generating a depth map based on the first scene signal and the second scene signal includes generating a depth map for each pixel of the first photodetector and the second photodetector.

11. The endoscopic system of claim 7, wherein estimating the scene-specific brightness non-uniformity correction includes:
estimating a first scene-specific brightness non-uniformity correction based on a detected first scene depth of the first photodetector and a first endoscopic system brightness non-uniformity profile of the first photodetector; and
estimating a second scene-specific brightness non-uniformity correction based on a detected second scene depth of the second photodetector and a second endoscopic system brightness non-uniformity profile of the second photodetector.

12. The endoscopic system of claim 1, wherein the endoscopic system brightness non-uniformity profile is based on a plurality of images generated by the photodetector with varying scene depths and varying orientations within the endoscopic system field of view.

13. The endoscopic system of claim 1, wherein the endoscopic system brightness non-uniformity profile is based on:
empirically estimating system brightness non-uniformity at a nominal scene depth; and
extrapolating to other working distances using a theoretical estimate of illumination drop-off with distance.

14. The endoscopic system of claim 1, wherein displaying the image of the scene includes adjusting raw image data based on the scene signal with the scene-specific brightness non-uniformity correction.

15. A non-transitory, machine-readable storage medium having instructions stored thereon, which when executed by a processing system, cause the processing system to perform operations comprising:
- illuminating a scene with a light source of an endoscopic system;
- generating a scene signal with a photodetector based on illumination light reflected off of the scene;
- detecting a scene depth across an endoscopic system field of view;
- estimating a scene-specific brightness non-uniformity correction based on the detected scene depth and an endoscopic system brightness non-uniformity profile; and
- displaying an image of the scene with a display of the endoscopic system based on the scene signal, the detected scene depth, and the scene-specific brightness non-uniformity correction.

16. The non-transitory, machine-readable storage medium of claim 15, further comprising instructions stored thereon, which when executed by the processing system, cause the processing system to perform operations comprising:
- emitting structured light from the light source, wherein detecting the scene depth across the field of view is based upon structured light reflected off of the scene.

17. The non-transitory, machine-readable storage medium of claim 16, wherein the structured light includes non-visible light.

18. The non-transitory, machine-readable storage medium of claim 16, further comprising instructions stored thereon, which when executed by the processing system, cause the processing system to perform operations comprising:
- emitting the illumination light in a first time interval; and
- emitting the structured light in a second time interval not overlapping with the first time interval.

19. The non-transitory, machine-readable storage medium of claim 15, wherein detecting the scene depth across the field of view of the endoscopic system includes co-registering a first scene signal of the photodetector and a second scene signal of a second photodetector of the endoscopic system; establishing a correspondence between the first scene signal and the second scene signal; and generating a depth map based on the first scene signal and the second scene signal.

20. A method for correcting brightness non-uniformity of an endoscopic system, the method comprising:
- illuminating a scene with a light source of an endoscopic system;
- generating a scene signal with a photodetector based on illumination light reflected off of the scene;
- detecting a scene depth across an endoscopic system field of view;
- estimating a scene-specific brightness non-uniformity correction based on the detected scene depth and an endoscopic system brightness non-uniformity profile; and
- displaying an image of the scene with a display of the endoscopic system based on the scene signal, the detected scene depth, and the scene-specific brightness non-uniformity correction.

* * * * *